United States Patent [19]

Snary

[11] 4,341,697

[45] Jul. 27, 1982

[54] ANTIGENIC MATERIAL

[75] Inventor: David Snary, Orpington, England

[73] Assignee: Burroughs Wellcome Co., Research Triangle Park, N.C.

[21] Appl. No.: 264,637

[22] Filed: May 18, 1981

Related U.S. Application Data

[62] Division of Ser. No. 134,262, Mar. 26, 1980, Pat. No. 4,298,596.

[30] Foreign Application Priority Data

Mar. 29, 1979 [GB] United Kingdom ................ 7911049

[51] Int. Cl.³ .............................................. C07G 7/00
[52] U.S. Cl. ............................................... 260/112 R
[58] Field of Search ....................... 260/112 R; 424/88

[56] References Cited

U.S. PATENT DOCUMENTS 3,911,097 10/1975 Hanson ................................ 424/12

4,298,596 11/1981 Snary .................................... 424/88

OTHER PUBLICATIONS

Scott & Snary, Nature, vol. 282, pp. 73–74, Nov. 1979.
Gottlieb, M., Journal of Immunology, vol. 119, No. 2, pp. 465–470, Aug. 1977.
Chem. Abstr., 91: 2327q, Apr. 1979.
Cross, G., Nature, vol. 277, pp. 310–312, Jan. 1979.

*Primary Examiner*—Allan Lieberman
*Assistant Examiner*—P. Short
*Attorney, Agent, or Firm*—Donald Brown

[57] ABSTRACT

A novel, glycoprotein antigen obtained from *T. cruzi* organisms can be used in vaccines for inducing immunity in humans to Chagas' disease. The glycoprotein is extracted by treating trypanosomes with a detergent and separating it from the cell debris and other proteinaceous material by affinity chromatography using lectin with affinity for glucose, mannose or galactose.

8 Claims, No Drawings

ANTIGENIC MATERIAL

This is a division, of application Ser. No. 134,262 filed Mar. 26, 1980, now U.S. Pat. No. 4,298,596.

The present invention relates to vaccines against Chagas disease. In particular it relates to antigenic material enriched in glycoproteins obtained from epimastigotes of *T. cruzi* and a process for producing the same.

Chagas' disease is endemic in several countries of Central and South America, especially Mexico, Brazil, Chile, Argentina and Venezuela. It is caused by the osmotrophic protozoan, *Trypanosoma cruzi*, which is transmitted by the common, blood sucking, reduvid bugs between vertebrate hosts such as man, domestic pets including cats and dogs, and wild mammals. Chagas' disease is especially dangerous because there are no satisfactory prophylactic or curative agents available and because an individual, once he has contracted the disease remains infected for life.

Because of the present lack of effective chemotherapy, several attempts have been made to develope vaccines for immunisation against Chagas' disease.

*T. cruzi* are known to exist in a number of different morphological stages depending upon their environment. In the infected mammal *T. cruzi* occur as typomastigotes and amastigotes while in the insect vector or in axenic culture in vitro, they may be induced to change into the epimastigote stage. This latter stage is relatively easily grown and has been utilised for many years in the production of antigen for immunological and diagnostic studies.

Several methods have been employed to prepare antigens from *T. cruzi*. Antigens prepared using mechanical rupture of *T. cruzi* organisms by freezethawing, trituration with or without beads, and sonication partially protect mice from acute trypanasomiasis (Johnson P., and Neal, R. A., Nature (1963), 200, 83; Goble F. C. et al., J. Parasitol, (1964), 50(Supple), 19; Seneca, H. et al. Nature, (1966), 209, 309–310; However, generally a decrease in parasitaemia but little increase in survival was observed. Homogenisation of epimastigotes of *T. cruzi*, at 140 atm. pressure in a nitrogen atmosphere with precise temperature control, preserved the subcellular structures intact and permitted their isolation (Segura, E. L. et al. J. Protozool, 21, 571–574). Subsequent to this work, Gonzalez-Cappa S. M. et al. (J. Parasitology 1976, 62, 130) and Segura, E. L. et al. (Ibid. 131) disrupted epimastigotes of *T. cruzi* by nitrogen cavitation and fractionated the homogenate by centrifugation. They discovered that protective activity was closely related with the flagellar fraction which afforded 90% survival of mice. The other fractions showed some activity, but was not as efficient as the flagellar fraction.

Unfortunately it has been noticed that many of these antigens, especially the flagellar fractions, although providing a degree of immunity to Chagas' disease, may cause symptons of the disease which have been associated with auto-immune effects (Texeira A. R. L. et al. Am. J. Pathol., (1975) 80, 163–180). For this reason is probable that simple sub-cellular fractions are unsuitable for use in vaccines.

Seneca has described a polysaccharide-containing antigen, isolated from *T. cruzi* organisms, (Nature, 209, 309, (1966)) and known as "chagastoxin". Recent work has shown chagastoxin to be a complex of "lipopeptidophosphoglycan" and several other components (Colli et al, J. Protozool, 21, 575, (1974); *FEBS Letters*, 52, 188, (1975); Biochem, Biophys. Acta. 444, 85, (1976); Eur. J. Bicohem., 74, 263, (1977); Gottlieb, J. Immunol., 119, 465, (1977)) but these are now known not to be protective against experimental Chagas' disease (Colli et al., Rev. Inst. Med. Trop. Sao Paulo, 20, 246, (1978) and Gottlieb, oral communication during the International Congress of Protozoology, New York, 1977).

A soluble polysaccharide antigen was isolated by Goncalves and Yamaha (J. Trop. Med. Hyg., 72, 39, (1969)) and Bergendi et al. (Exp. Parasitol. 28, 258 (1970)) but there is no indication that this is protective against Chagas' disease.

It has now been found that protein fractions obtained from cultured epimastigotes and containing certain glycoproteins are useful in inducing immunity to Chagas' disease.

It appears that the glycoprotein fraction produced by the method described below is free from the crossreacting determinants that are thought to cause the autoimmune phenomena found in infected individuals. The presence of such determinants in epimastigotes and fractions thereof may be demonstrated by testing for interaction of the epimastigote or a fraction thereof with components which can recognise heart tissue in the antisera of patients suffering from chronic Chagas' disease.

According to the present invention there is provided an antigen which contains glycoproteins of molecular weight within the range from 6 to $9.5 \times 10^4$ obtained from *T. cruzi* organisms, the glycoproteins being substantially insoluble in water and capable of interacting with lactins which have an affinity for glucose, mannose or galactose, the antigen being substantially free from non-proteinaceous matter.

The molecular weight of the above-mentioned proteins can be estimated conveniently using polyacrylamide gel electrophoresis techniques (Laemmli, U. K., Nature (Lond.), (1970), 227,680–685).

The glycoprotein of the present invention is effectively insoluble in water. However, when isolated according to the process disclosed below, the glycoprotein fraction may acceptably be associated with up to 5% by weight of water-soluble material of non-proteinaceous nature.

Lectins are proteinaceous materials capable of interacting with certain sugar moieties, e.g. glucose units, while having no appreciable interaction with other sugars. They mare therefore be used for distinguishing which types of sugar are present in a glycoside such as glycoprotein. The glycoproteins of the present invention are capable of interacting with those lectins which are known to have an affinity for glucose, mannose or galactose moieties.

The antigenic glycoprotein is a relatively fragile molecule, and is susceptable to breakdown by proteases also found in *T. cruzi*. Accordingly, care must be exercised in the extraction and purification of the antigen.

According to a second aspect of the present invention there is provided a process for extracting and purifying the above-mentioned antigen comprising of the steps of
 (a) harvesting trypanosmes from a culture;
 (b) solubilising the antigen and
 (c) removing substantially all non-glycoproteinaceous proteins by affinity chromatography using lectins with affinity for glucose, mannose or galactose.

The antigen is found in all stages of *T. cruzi,* however it is convenient to produce it from epimastigotes as this stage can most easily be cultured. Epimastigotes are advantageously grown in Bone and Parents medium from trypomastigotes contained in a blood sample taken from an infected animal. The epimastigotes are maintained by serial passage in that medium with 5% rabbit serum, penicillin (200 units/ml) and streptomycin (100 units/ml), but other culture media may be used such as Lit (modified) medium at 28° C. (Gutteridge et. al. J. Protozoology; 21; 5127; (1969). Trypomastigotes and amastigotes may be obtained from infected animals or cultured in vitro, e.g., using the method of Stohlman et al Arch Microbiol; 9; 301–311; (1973).

Advantageously, amastigotes may be grown in vitro at 37° C. in the presence of the mouse muscle sarcoma cell line 52 in Dulbecco's modified Eagles medium containing 10% foetal calf serum, penicillin and streptomycin.

In step (a) the trypanosomes may conveniently be harvested by low speed centrifugation, preferably below 8000 g min since greater forces tend to cause the break-down of the antigen, preferably at between 200 g and 600 g for 10 minutes and most preferably at about 400 g for 10 minutes. The cells are then washed with phosphate buffered (pH 7.2) saline (PBS).

Conditions for centrifugation are expressed in units of g min, that is the force applied by the duration of the force. Thus 4000 g min encompasses conditions such as 400 g for 10 minutes as well as 2000 g for 2 minutes and so on within reasonable limits. Certain conditions within the generality have been found particularly advantageous and these are expressed specifically as for instance 400 g for 10 minutes.

In step (b) the antigen may be solubilised by the addition of detergent to a suspension of the cells in PBS. No specific time or temperature is required for solubilisation, but 5 minutes at 0° C. has been found convenient for a suspension of $5\times10^8$ cells/ml.

Detergents may be of the ionic or non-ionic type. However use of the ionic detergents may promote the formation of DNA gels and non-ionic detergents are therefore more convenient. Examples of non-ionic detergents are Nonidet P 40, Triton X-100 and Brij 99. (Registered Trade Marks, manufactured by Shell, Rohn and Hass Co. and I.C.I. respectively) and a polyoxyethylene (12) tridecyl ether detergent, e.g. Renex 30 (Registered Trade Mark, Manufactured by Honeywell Atlas Limited,) which is the most preferred detergent. Detergent is added to a final concentration of between 1 and 5% preferably about 2% v/v.

Other undesirable proteins are removed in step (c) for instance by affinity chromatography using lectins (see, for instance Hayman M. J. and Crumpton M. J., Biochem and Biophys Research Comms, 47, 923, (1972)) which possess affinity for glucose, mannose or galactose. Concanavalin A or lectins from *Ricinis communis* are suitable for this purpose. Lectin obtained from *Lens Culinaris* with affinity for glucose and mannose is most preferred.

The lectins are prepared for use in affinity chromatography columns by linking the protein to an inert support such as Sepharose 4b activated with cyanogen bromide. After application of the antigen from step (b) to the affinity column, non-glycoproteinaceous material is washed through the column with an eluant solution containing detergent. The eluant may advantageously contain buffers and salts, conveniently 0.15 M sodium chloride and 0.01 M tris-hyrochloride pH 7.4 buffer are used, but these may be omitted or used at other concentrations, and other buffers and salts may be used provided that extremes of pH and high salt concentrations are avoided. The desired glycoprotein is eluted from the column by addition of a sugar to the eluant, to a concentration of 1% to 4% preferably 2% w/v of eluant is used, sugars such as glucose or mannose or their derivatives may be employed, however it is preferred that methyl mannoside is used. Alternatively the glycoprotein may be recovered by denaturing the lectin, e.g. using concentrated sodium dodecyl sulphate solution.

The purification process may be improved by the optional step of removing cell debris before affinity chromatography. It has been found convenient to use centrifugation at about 450,000 g min. Preferably about 15,000 g for 30 minutes although somewhat higher or lower speeds providing forces down to about 3000 g for 30 minutes may also be employed. Alternatively the cell debris can be removed by filtration.

The yield of antigen may be enhanced by the addition, to the cell suspension, of protease inhibitors, either before step (b) or at the same time as the addition of detergent. While these inhibitors may be omitted on small scale production of the antigen, on larger scales, it is more important that proteolysis is prevented otherwise most of the antigen will be destroyed during the prolonged purification procedure. Protease inhibitors also protect the lectin affinity columns, allowing re-use of the columns which would otherwise be damaged by proteases.

There are three classes of protease inhibitors; those which inhibit proteases in general, those which are specific for serine proteases and those which are specific for sulphydryl proteases. General inhibitors are exemplified by aprotinin, metal cleaning agents such as ethylenediamine tetracetate (EDTA) and metal ions such as mercury or zinc ions. Inhibitors of serine proteases include tosyl-L-lysine chloromethyl keytone hydrochloride (TLCK), phenylmethylsulphonic fluoride, and di-isopropyl fluorophosphate. Iodoacetamide, iodoacetic acid or p-chloromercuri benzoate are examples of sulphydryl proteases inhibitors. There are many other inhibitors of proteases which are known in the literature, however it is found convenient to use aprotinin, TLCK and iodacetamide, and these are the most preferred inhibitors. Concentrations of aprotinin of 2 to 10, preferably about 5 units/ml, of TLCK of 0.5 to 2 mM, preferably 1 mM and of iodoacetamide of 5 to 20 mM preferably about 10 mM are particularly recomended.

When used to asses the purity of the antigen polyacrylamide gel electrophoresis shows that the glycoprotein eluted from the affinity column comprises a plurality of components of estimated molecular weight between 6 and $9.5\times10^4$. The most preferred glycoprotein has a molecular weight of about $9\times10^4$ and the other components of the antigen are fragments of this glycoprotein. The antigen could be further purified by known techniques, however the effort and concomitant loss of antigen is normally unnecessary and wasteful as these glycoprotein fragments retain their antigenicity.

The antigen may be used in the form eluted from the affinity column, or may be further processed, such as by precipitation with an organic solvent such as an alcohol, e.g. ethanol and then resuspended as a particulate, or solubilised by addition of detergent solution. Such further steps, whilst producing more highly purified antigen also cause a reduction in the overall yield of the antigen.

The concentration of solutions of the antigen may be estimated, for instance, by spectrophotometry. Conveniently the absorption at 280 nm may be measured and the concentration of the antigen is then determined using the extinction coefficient of 1.2 for a solution of 1 mg of protein per ml.

The antigen described above may be incorporated into a vaccine for inducing immunity to Chagas' disease in susceptible hosts such as mammals, including humans, at risk to be infected by *T. cruzi* for this purpose the antigen may be presented in association with a pharmaceutically acceptable carrier.

According to the present invention in a further aspect there is provided a vaccine for inducing immunity to Chagas' disease which comprises an antigen as hereinbefore defined in association with a pharmaceutically acceptable carrier.

Pharmaceutically acceptable carriers, in this instance, are liquid media suitable for use as vehicles to introduce the antigen into the patient. An example of such a carrier is saline solution. The antigen may be suspended as a solid in the carrier, or it may be solubilised by the addition of pharmaceutically acceptable detergent.

The vaccine may also comprise an adjuvant for stimulating the immune response and thereby enhancing the effect of the vaccine. Convenient adjuvants for use in the present invention include Freunds complete adjuvant and more particularly, saponin *Corynebacterium parvum* (coparvax) and aluminium hydroxide or a mixture of these or other known adjuvants.

Conveniently the vaccines are formulated to contain a final concentration of antigen in the range of from 0.2 to 5, preferably 0.5 to 2, most preferably 1, mg/ml. After formulation the vaccine may be incorporated into a sterile container which is then sealed and stored at a low temperature, for example 4° C., or may be freeze dried.

In order to induce immunity in humans to Chagas' disease one or more doses of the vaccine, formulated as described above, may be administered. It is recommended that each dose is 0.1 to 2 ml preferably 0.2 to 1 ml, most preferably 0.5 ml of vaccine.

The present invention in a further aspect provides a method for inducing immunity to Chagas' disease in susceptible hosts, comprising the administration of an effective amount of a vaccine, as hereinbefore defined, to the host.

An effective amount of the vaccine is that quantity which is sufficient to induce, in the host animal, immunity to Chagas' disease.

The vaccines of the present invention are desireably administered by subcutaneous or intramuscular injection although the intravenous route may be employed. The treatment may consist of a single dose of vaccine or a plurality of doses over a period of time. An advantageous treatment schedule requires adminstration of two doses of vaccine with an interval of 7 to 56, preferably 14 days between doses. If longer protection is required, booster doses may be administered after longer intervals, for instance, annually.

The following Examples serve to illustrate the invention but are not intended to limit it in any way.

EXAMPLE 1

Extraction and Purification of Antigen

Trypomastigotes were obtained in a blood sample from an infected animal and cultured in Bone and Parent's liquid medium (Bone. G. J. et al.; J. Gen. Microbiol.; 31, 261–266; (1963)) with 5% rabbit serum, penicillin (to 200 units/ml) and streptomycin (to 100 units/ml) added whereupon they developed into epimastigotes which were maintained by serial passage in Bone and Parents medium.

Cultures were established with $1 \times 10^7$ epimastigotes/ml and incubated at 26° C. for 4–7 days in glass bottles containing the medium (1000 ml) with gentle agitation. At the end of the culture period the medium contained ca. $2 \times 10^8$ epimastigotes/ml. These were separated from the supernatant by centrifugation at 400 g for 10 minutes and washed with phosphate-buffered (pH 7.2) saline (PBS). The pellet was resuspended in PBS. ($5 \times 10^8$ epimastigotes/ml) and detergent (Renex 30) (to 2% v/v), aprotinin (to 5 units/ml), tosyl-L-lysinechloromethyl ketone hydrochloride (TLCK) (to 1 mL) and iodoacetamide (to 10 mM) were added to the suspension. The suspension was maintained at 0° C. for five minutes then centrifuged (15,000 g for 30 min) to remove the cell debris.

The supernatant (200 ml containing the product of $2 \times 10^{11}$ cells) was applied to the top of an affinity chromatography column ($2.5 \times 10$ cm containing *Lens culinaris*, glucose- and mannose-binding lectin supported on cyanogen bromide activated Sepharose 4b at 10 mg protein/ml Sepharose) and pre-washed extensively with detergent solution (1% v/v Renex 30, 10 column volumes) containing sodium chloride (0.15 M) and tris-hydrochloride buffer (0.01 M, pH 7.4). the antigen was then eluted using methyl mannoside solution (2% w/v) containing detergent (1% v/v Renex 30), salt (0.15 M sodium chloride) and buffer (0.01 M tris hydrochloride pH 7.4) until no further glycoprotein was eluted (as shown by absorption at 280 nm). The glycoprotein in the first 20 ml of methyl mannoside solution to run off the column.

The eluate was collected and the antigen precipitated by adding ethanol (3 volumes) and allowing it to stand at $-20°$ C. for 48 hours. The precipitate was recovered by centrifugation at 2500 g for 15 min, affording 10 mg of the glycoprotein.

The purity of the glycoprotein fraction was assayed by polyacrylamide gel electrophoresis.

EXAMPLE 2

Preparation of a vaccine

The precipitate of Example 1 was resuspended in saline solution (0.9% w/v) and emulsified with an equal volume of Freunds complete adjuvant. The vaccine represented a 0.1% w/v suspension of glycoprotein.

EXAMPLE 3

Protection Studies

Groups of 10, $C_{57}BL$ mice were immunised intraperitoneally and/or subcutaneously with 100 μl doses of the vaccine of Example 2 at days 0 and 14. Control mice were either untreated or received Freunds complete adjuvant alone.

The mice were challenged on day 28 with $5 \times 10^3$ blood stream trypomastigotes of *T. cruzi*. All control mice died (mean survival time 21 days, peak parasitaemia $3 \times 10^7$ parasites/ml of blood) whilst the immunised mice were all still alive on day 61 when the experiment was terminated. In these latter groups peak parasitaemia, at day 21, was $5 \times 10^5$ parasites/ml of blood, and there were no microscopically detectable parasites after day 38.

I claim:

1. An antigen obtained from *T. cruzi* organisms comprising glycoprotein of molecular weight from about $6 \times 10^4$ to about $9.5 \times 10^4$, said glycoprotein being substantially insoluble in water and being capable of interacting with lectins which have an affinity for glucose, mannose or galactose, said antigen being substantially free from non-proteinaceous matter.

2. An antigen according to claim 1 wherein said glycoprotein has molecular weight of about $9 \times 10^4$ when estimated by polyacrylamide gel electrophoresis.

3. A process for extracting and purifying the antigen of claim 1 comprising the steps of (a) harvesting the trypanosomes from a culture;
(b) solubilising the antigen and
(c) removing substantially all non-glycoproteinaceous proteins by affinity chromatography using lectins with affinity for glucose, mannose or galactose.

4. A process according to claim 3 comprising the additional step of removing cell debris prior to step (c).

5. A process according to claim 3 or claim 4 wherein the trypanosomes are epimastigotes.

6. A process according to claim 3 or claim 4 wherein the antigen is solubilised by the addition of non-ionic detergent.

7. A process according to claim 3 or claim 4 wherein affinity chromatography is conducted using Concanavalin A or lectin obtained from *Ricinis communis* or *Lens cullinaris* with affinity for glucose and mannose.

8. A process according to claim 3 or claim 4 wherein either before or at the same time as step (b) is carried out a protease inhibitor is added to the antigen.

* * * * *